(12) United States Patent
Bashan et al.

(10) Patent No.: US 11,395,610 B2
(45) Date of Patent: Jul. 26, 2022

(54) DEVICE, SYSTEM AND METHOD FOR NON-INVASIVE MONITORING OF PHYSIOLOGICAL MEASUREMENTS

(71) Applicant: WEAR2B LTD., Rosh Pina (IL)

(72) Inventors: Ohad Bashan, Sde Varburg (IL); Giora Bar-Sakai, Tel Aviv (IL); Oded Bashan, Rosh Pina (IL); Ben Zion Dekel, Hadera (IL)

(73) Assignee: Wear2B Ltd., Rosh Pina (IL)

( * ) Notice: Subject to any disclaimer, the term of this patent is extended or adjusted under 35 U.S.C. 154(b) by 0 days.

(21) Appl. No.: 16/638,481

(22) PCT Filed: Aug. 16, 2018

(86) PCT No.: PCT/IL2018/050907
§ 371 (c)(1),
(2) Date: Feb. 12, 2020

(87) PCT Pub. No.: WO2019/035133
PCT Pub. Date: Feb. 21, 2019

(65) Prior Publication Data
US 2020/0261005 A1    Aug. 20, 2020

Related U.S. Application Data

(60) Provisional application No. 62/546,565, filed on Aug. 17, 2017.

(51) Int. Cl.
*A61B 5/1455* (2006.01)
*A61B 5/145* (2006.01)

(52) U.S. Cl.
CPC ...... *A61B 5/14558* (2013.01); *A61B 5/14532* (2013.01); *A61B 5/14546* (2013.01); *A61B 2562/0238* (2013.01)

(58) Field of Classification Search
CPC ... A61B 5/0205; A61B 5/0059; A61B 5/1455; A61B 5/14551; A61B 5/14552;
(Continued)

(56) References Cited

U.S. PATENT DOCUMENTS 6,437,856 B1    8/2002  Jacques
2008/0219522 A1*  9/2008  Hook ................. G06V 40/1394
                                                                    382/124
(Continued)

FOREIGN PATENT DOCUMENTS

EP        2205949        5/2009
WO    WO 2017/115361    7/2017

OTHER PUBLICATIONS

International Search Report and Written Opinion in corresponding PCT App No. PCT/IL2018/050907, dated Dec. 10, 2018.
(Continued)

*Primary Examiner* — Chu Chuan Liu
(74) *Attorney, Agent, or Firm* — Pearl Cohen Zedek Latzer Baratz LLP

(57) ABSTRACT

A device, system and method of non-invasive monitoring of physiological measurements of a subject are disclosed. The method may include: emitting light beams towards skin of the subject, with at least one light source having at least one predetermined polarization, wherein the light beams are emitted at an angle $0° \leq \alpha < 90°$ relative to the normal to the skin surface of the subject; sensing light beams with at least one light sensor positioned at a predetermined distance from the at least one light emitting source; filtering out signals corresponding to detected light beams based on the at least one predetermined polarization of the at least one light source; and determining at least one physiological signal, based on the sensed light beams after filtering. The sensed
(Continued)

light beams may pass through at least one of epidermis, dermis, subcutaneous tissue and blood vessel of the subject.

12 Claims, 3 Drawing Sheets

(58) Field of Classification Search
CPC ............ A61B 5/14558; A61B 5/14532; A61B 5/14546; A61B 2562/0238; A61B 2562/0233
See application file for complete search history.

(56) References Cited

U.S. PATENT DOCUMENTS

| | | | |
|---|---|---|---|
| 2013/0085351 A1* | 4/2013 | Kudavelly | A61B 5/14558 600/315 |
| 2013/0289413 A1* | 10/2013 | Ochs | A61B 5/743 600/476 |
| 2014/0350365 A1 | 11/2014 | Sato | |
| 2015/0099943 A1* | 4/2015 | Russell | A61B 5/0059 600/301 |
| 2015/0196233 A1* | 7/2015 | Gerlitz | A61B 5/0059 600/301 |
| 2015/0238636 A1* | 8/2015 | Homyk | G01N 33/588 600/317 |

OTHER PUBLICATIONS

Search Report for European Application No. 18846064.6, dated Apr. 19, 2021.

* cited by examiner

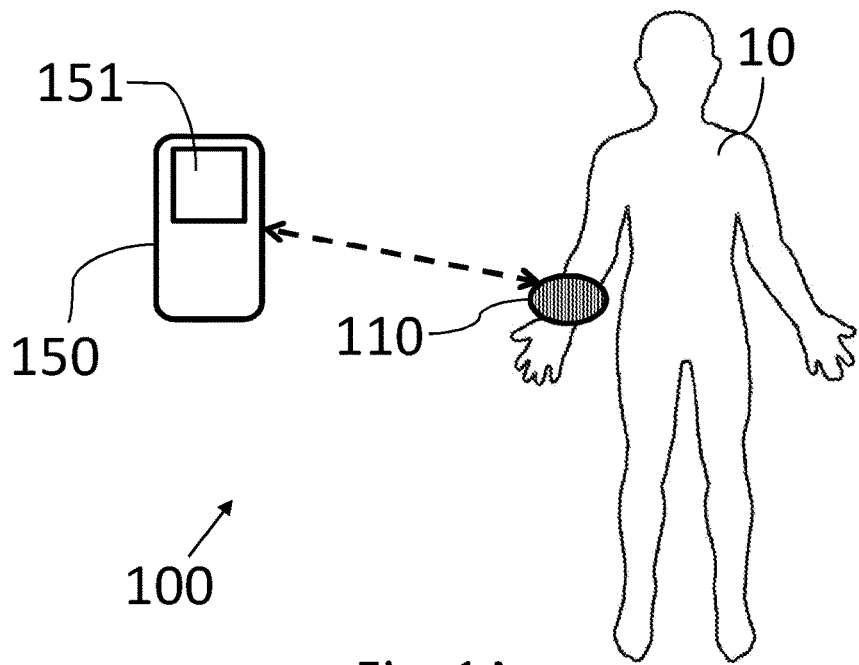
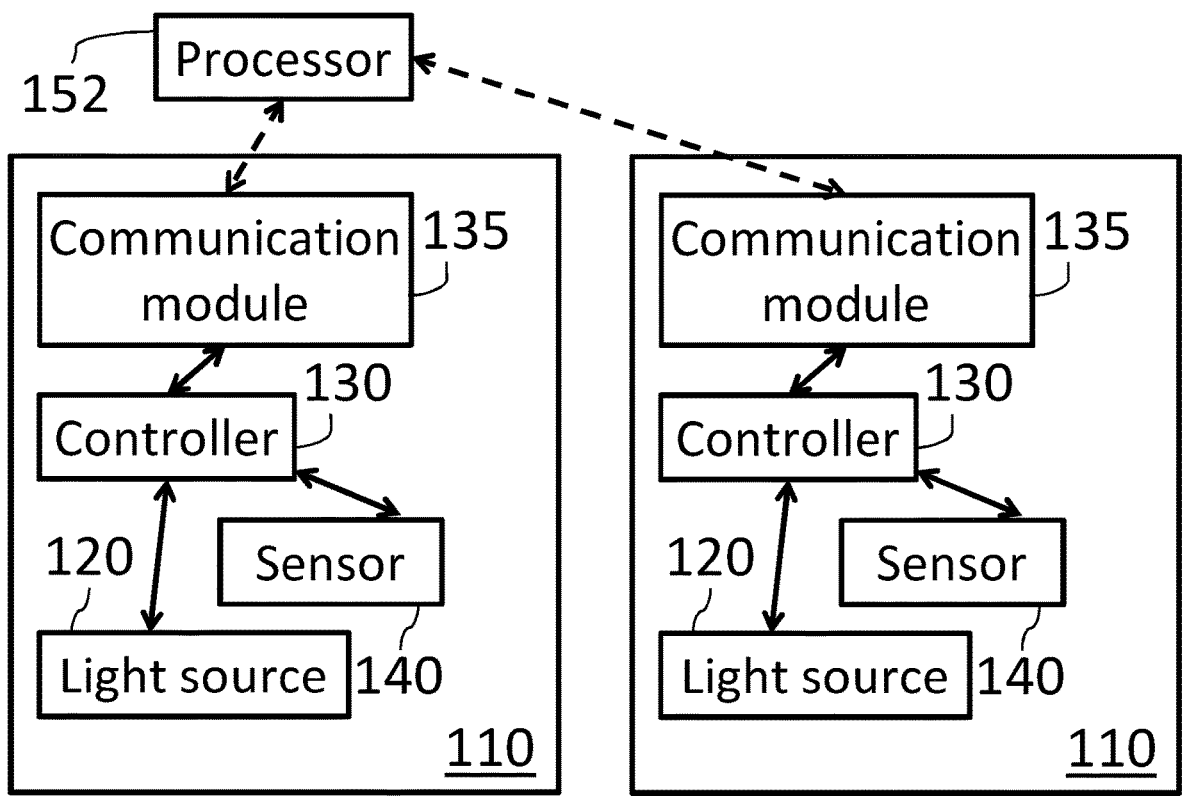
Fig. 1A
Fig. 1B

DEVICE, SYSTEM AND METHOD FOR NON-INVASIVE MONITORING OF PHYSIOLOGICAL MEASUREMENTS

CROSS-REFERENCE TO RELATED APPLICATIONS

This application is a National Phase Application of PCT International No. PCT/IL 2018/050907 Filing Date Aug. 16, 2018, entitled, "DEVICE, SYSTEM AND METHOD FOR NONINVASIVE MONITORING OF PHYSIOLOGICAL MEASUREMENTS", published on Feb. 21, 2019, under PCT International Application Publication No. WO 2019/035133 which claims the benefit of U.S. Provisional Patent Application No. 62/546,565, filed Aug. 17, 2017 which is hereby incorporated by reference.

FIELD OF THE INVENTION

The present invention generally relates to non-invasive physiological measurements. More particularly, the present invention relates to wearable devices, systems and methods for non-invasive monitoring and analyzing of physiological measurements.

BACKGROUND OF THE INVENTION

Many people periodically undergo physical checks in order to monitor any change in their health. For instance, checks may include taking periodic (e.g., monthly) blood tests to check cholesterol levels in the blood, or daily glucose tests with a dedicated device (typically requiring skin puncturing) so as to monitor the glucose levels in the blood.

Since these tests may be invasive and sometimes painful to the patient, a need arises for a non-invasive solution that could allow users to continuously monitor their physiological characteristics as well as identify trends and changes in the levels of the measured parameters in the blood. Some commercially available products allow non-invasive measurements of physiological signs such as pulse or temperature, however these solutions are not very accurate and there is no available solution to replace the current invasive measurements, capable of measuring levels of blood components in a non-invasive manner. Particularly, most available solutions usually suffer from a low signal to noise ratio that reduce the accuracy of the measurements.

SUMMARY OF THE INVENTION

Some aspects of the invention may be directed to a device, system and method of non-invasive monitoring of physiological measurements of a subject. In some embodiments, the method may include: emitting light beams towards skin of the subject, with at least one light source having at least one predetermined polarization, wherein the light beams are emitted at an angle $0° \leq \alpha < 90°$ relative to the normal to the skin surface of the subject; sensing light beams with at least one light sensor positioned at a predetermined distance from the at least one light emitting source; filtering out signals corresponding to detected light beams based on the at least one predetermined polarization of the at least one light source; and determining at least one physiological signal, based on the sensed light beams after filtering. In some embodiments, the sensed light beams may pass through at least one of epidermis, dermis, subcutaneous tissue and blood vessel of the subject.

In some embodiments, emitting the light beams may be from a first light source having a first polarization and a second light source having a second polarization. In some embodiments, sensing light beams may be with one or more light sensor configured to detect light at the first polarization and the second polarization. In some embodiments, the filtering may be carried out with a wire grid. In some embodiments, the sensing may be carried out at an angle $0° \leq \beta < 90°$ relative to the normal to the skin surface of the subject. In some embodiments, the light beams may be emitted at an angle $40° \leq \alpha < 50°$ degrees. In some embodiments, the sensing is carried out at an angle $40° \leq \beta < 50°$ relative to the normal to the skin surface of the subject.

In some embodiments, the method may further include modulating at least one of the emitted light beams and the sensed light beams to a predetermined frequency. In some embodiments, filtering out signals may include filtering signals having the at least one predetermined polarization. In some embodiments, the method may further include emitting light beams in at least one predetermined wavelength and determining the at least one physiological signal may be also based on the at least one predetermined wavelength. In some embodiments, sensing the physiological signals of the subject may be carried out repetitively every predefined time period.

In some embodiments, the method may further include comparing at least two consecutive measurements to detect a change. In some embodiments, the method may further include calibrating intensities of light beams detected by the at least one light sensor, wherein the detected light beams may be reflected from a known blood vessel and detected thereon. In some embodiments, the method may further include positioning the at least one of light sensor and light source over a known blood vessel. In some embodiments, the method may further include controlling the polarization of the emitted light beams. In some embodiments, the method may further include issuing an alert upon detection of a change in measured physiological signals exceeding a predetermined threshold.

Some aspect of the invention may be directed to a monitoring device adapted to be removably attachable to a subject's body. In some embodiments the device may include: a measuring unit that includes: at least one light emitting source, configured to emit light beams in at least one predetermined polarization at at least one predetermined first angle between the emitted light beam and the normal to the skin surface of the subject; at least one sensor, located at predetermined distances from the at least one light emitting source, wherein the at least one sensor is configured to detect light beams emitted from the at least one light emitting source at least one predetermined second angle between the reflected light beam and the normal to the skin surface of the subject; and at least one polarizer, coupled to the at least one sensor and configured to filter out light beams correspond to the at least one polarization of the at least one light emitting source. The monitoring device may further include a controller, coupled to the measuring unit, and configured to receive measurements of the detect light beams and analyze physiological signs of the subject based on the detected light beams to determine at least one physiological signal. In some embodiments, the detected light beams may pass through at least one of dermis, subcutaneous tissue and blood vessel of the subject.

In some embodiments, the at least one predetermined first angle is an angle of $0° \leq \alpha < 90°$ between the emitted light beam and the normal to the skin surface of the subject.

In some embodiments, the at least one predetermined first angle may be an angle of 40°≤α<50° between the emitted light beam and the normal to the skin surface of the subject. In some embodiments, the at least one predetermined second angle may be an angle of 0°≤β<90° between the reflected light beam and the normal to the skin surface of the subject. In some embodiments, the at least one predetermined second angle may be an angle 40°≤β<50° relative to the normal to the skin surface of the subject.

In some embodiments, the at least one polarizer may be configured to filter out signals having the at least one predetermined polarization. In some embodiments, the monitoring device may be wearable. In some embodiments, the device further includes a first light source configured to emit light at a first polarization; and a second light source configured to emit light at a second polarization. In some embodiments, a first polarizer may be coupled to the at least one sensor for filtering the first polarization; and a second polarizer may be coupled to the at least one sensor for filtering the second polarization.

In some embodiments, the amount of light with polarization corresponding to the polarization of the at least one light emitting source that may be filtered out is in the range of 20-50%. In some embodiments, the at least one sensor may be configured to detect light beams for at least one predetermined angle. In some embodiments, the device may further include a modulating unit configured to modulate at least one of the emitted and received light beams to a predetermined frequency. In some embodiments, the controller may be configured to control the modulating unit. In some embodiments, the at least one light emitting source may be configured to emit light beams in at least one predetermined wavelength, and the at least one physiological signal is determined based on the at least one predetermined wavelength.

In some embodiments, the device may further include a communication module, configured to allow communication with external computerized devices, wherein the communication module is configured to allow wireless communication. In some embodiments, the device may further include a wire grid as the polarizer. In some embodiments, the controller may be configured to control the polarization of the at least one light emitting source.

A system for non-invasive monitoring of physiological measurements may include at least one monitoring device according to any embodiment disclosed herein and a processor, in communication with the at least one monitoring device, the processor may be configured to receive data from the at least one monitoring device and determine at least one physiological signal. In some embodiments, the monitoring device may be configured to be removably attachable to the subject's body, and wherein the sensed light beams pass through at least one of dermis, subcutaneous tissue and blood vessel of the subject.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A schematically illustrates a non-invasive monitoring system, according to some embodiments of the invention;

FIG. 1B schematically illustrates a block diagram of the non-invasive monitoring system, according to some embodiments of the invention;

Figure 2:
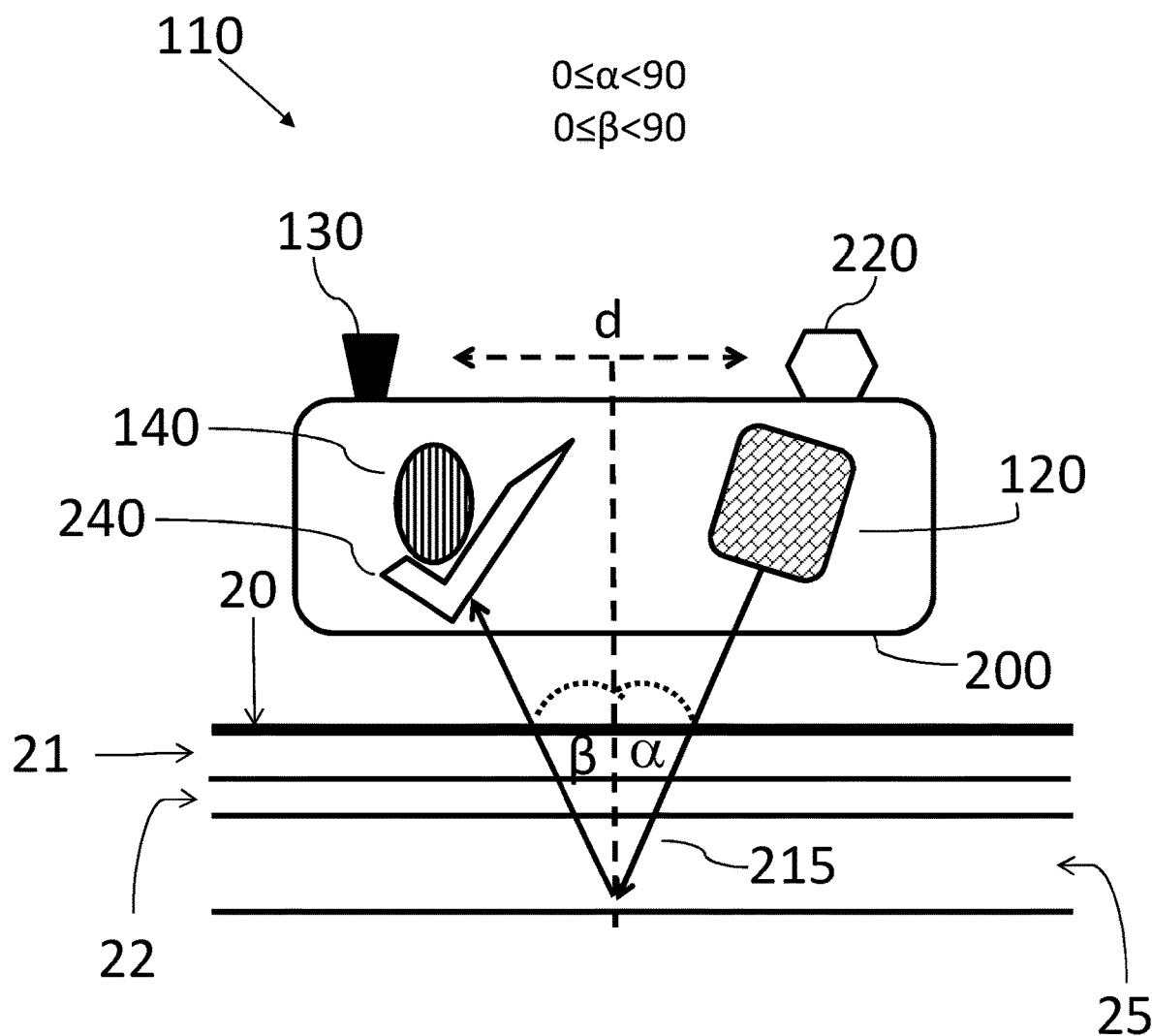
FIG. 2 schematically illustrates a cross-sectional view of a monitoring device, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the invention may be practiced without these specific details. In other instances, well-known methods, procedures, and components modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g. electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Reference is now made to FIG. 1A-1B, which schematically illustrates a non-invasive monitoring system 100 and a block diagram of the non-invasive monitoring system 100, respectively, according to some embodiments of the invention. It should be noted that the direction of arrows in FIG. 1 may indicate the direction of information flow.

The non-invasive monitoring system 100 may allow continuous and/or repetitive non-invasive monitoring of a subject 10, using a wearable monitoring device 110. In some embodiments, non-invasive monitoring system 100 may allow multi trajectory detection of spectral data in an inhomogeneous medium to extract the changes in chromophore concentration.

Non-invasive monitoring system 100 may include at least one monitoring device 110 configured to detect changes in measured physiological signals of subject 10, and a computerized device 150 (e.g., with a processor and memory unit) in the vicinity of subject 10 and/or a controller in a remote facility (such as a medical facility) in communication with the at least one monitoring device 110. The computerized device 150 may be configured to receive data (e.g., wirelessly, indicated with a dashed arrow) corresponding to measured physiological signals from the at least one monitoring device 110. According to some embodiments, a processor 152 of computerized device 150 may determine or calculate at least one physiological signal or value from detected light signals from monitoring device 110. For example, monitoring device 110 may detect reflected light beams and determine the received intensity to be sent (e.g., wirelessly) to computerized device 150 for further processing to determine at least one physiological signal (e.g., a glucose level may be determined or calculated). In some embodiments, monitoring device 110 may send all raw data to be processed by computerized device 150 to determine physiological signals.

In some embodiments, computerized device 150 may be or may include, for example, a mobile phone, a tablet, a personal computer, a mobile computer, or any other suitable computing device 150. For example, system 100 as described herein may include one or more devices such as computerized device 150. In some embodiments, the at least one monitoring device 110 may be removably attachable to the subject's body 10. In some embodiments, the at least one monitoring device 110 may be wearable on a limb of subject 10 and/or on other parts of the subject's body (e.g. on a finger).

It should be appreciated that wearable monitoring device 110 may continuously collect data on the physiological signals (e.g., pulse, blood components levels, subcutaneous tissue components level, etc.) of the subject 10, as long as monitoring device 110 is worn by (or otherwise attached to) the subject 10, and therefore monitoring device 110 may provide ongoing data such that changes (e.g., in time) in measured physiological signals may be detected. In some embodiments, monitoring device 110 may collect the data (e.g., and store in a dedicated memory) when monitoring device 110 is worn by the subject 10, and provide the collected data to the subject even when monitoring device 110 is not worn by the subject 10.

According to some embodiments, monitored data may be transferred from computerized device 150 to wearable monitoring device 110, and vice versa, via a compatible communication module 135 (e.g., via Wi-Fi, Bluetooth, near field communication (NFC), etc.). For example, a subject 10 wearing monitoring device 110 and also operating a mobile phone, may utilize the mobile phone as computerized device 150 in order to transfer data to and from wearable monitoring device 110 via wired and/or wireless communication.

In some embodiments, wearable monitoring device 110 may include a dedicated controller 130 coupled to a measuring unit 200 (as shown in FIG. 2) that may be configured to measure physiological signs of subject 10, and a power storage unit (e.g. a battery). For instance, computerized device 150 may include a compatible communication module, a display 151 (e.g. with a user interface), and a processor 152 capable of processing and monitoring the physiological data of subject 10 measured by measuring unit 200.

Computerized device 150 may have, according to some embodiments, a dedicated user interface (e.g. with a dedicated algorithm installed thereon) so as to display real-time measurements to subject 10. Thus, users (e.g., the subject, a caregiver and/or physician) may receive alerts and/or updates regarding the physiological signs that were measured by measuring unit 200 of the wearable monitoring device 110. In some embodiments, computerized device 150 may issue an alert (e.g., via display and/or speaker 151) upon detection of a change in measured physiological signals, for instance exceeding a predetermined threshold.

In some embodiments, processor 152 of computerized device 150 may communicate with at least one controller 130 of monitoring device 110 (e.g., via a communication module 135). Controller 130 of monitoring device 110 may operate at least one light emitting source 120 to emit light beams towards subject 10 and measure the returned light with at least one sensor 140 coupled to controller 130. Once a measurement is carried out, the measurement data may be analyzed by controller 130 of monitoring device 110 and/or processor 152 of computerized device 150. In some embodiments, at least one light emitting source 120 may emit polarized light beams towards subject 10 so as to increase signal to noise ratio, as further described hereinafter. In some embodiments, computerized device 150 may include a cloud based computerized device.

Reference is now made to FIG. 2, which schematically illustrates a cross-sectional view of a monitoring device 110 attached to the subject 10, according to some embodiments of the invention. In some embodiments, the direction of the arrows may indicate the direction of the light beams. In some embodiments, when in use, measuring unit 200 may be adjacent to and in contact with the skin of subject 10 so as to reduce noises from the environment. In some embodiments, multiple measuring units 200 may be employed (for instance as an array) in order to allow simultaneous monitoring of several blood vessels of the subject 10.

In some embodiments, measuring unit 200 may include at least one light emitting source 120, for example Laser, configured to emit light beams 215 having a predetermined polarization. In some embodiments, at least one light emitting source 120 may be a light source that is capable of producing a polarized light, for example: Laser Diode. In some embodiments, at least one light emitting source 120 may include a light source that emits nonpolarized light, for example, light emitting diodes (LED) and a polarizer attached to the light source for polarizing the emitted light. In some embodiments, measuring unit 200 may include two light emitting sources 120, a first light emitting sources 120 configured to emit light at a first polarization (e.g., an S polarization) and a second light emitting sources 120 configured to emit light at a second polarization (e.g., a P polarization). In some embodiments, the first and second light emitting sources 120 may be configured to emit light at the same wavelength or at different wavelength. In some embodiments, polarization of light beams 215 may be controlled, for instance by controller 130. In some embodiments, the at least one light emitting source 120 may be operated in different wavelengths, for instance in order to allow measurements of different features (e.g. glucose, insulin, low density lipoprotein (LDL), very-low density lipoprotein (VLDL) and Albumin). In some embodiments, measurements of different substances (e.g. glucose and Albumin) may be carried out with different wavelengths and/or different number of wavelengths.

In some embodiments, the measuring unit 200 may be removably attachable to the skin 20 of the subject 10, so as to emit light beams 215 with the at least one light emitting source 120 towards the skin 20. In some embodiments, at least one light emitting source 120 may be configured to emit light beams 125 at at least one predetermined first angle α. In some embodiments, the at least one predetermined first angle may be an angle 0°≤α<90° between the emitted light beam 215 and the normal to the skin surface 20 of the subject. For example, the measuring unit 200 may be positioned along a blood vessel 25 (e.g., on the wrist of the subject 10). Several layers may be identified below the skin 20 of the subject 10, for example Epidermis layer at 0-0.3 mm depth, a Dermis layer at 0.3-2 mm depth and a subcutaneous layer there below. In some embodiments, the polarized light beams may be emitted at an angle 0°≤α<90° degrees relative to the normal to the skin surface 20 of the subject (indicated 'α' in FIG. 2). In some embodiments, the at least one predetermined first angle α may be 40°≤α≤50° between the emitted light beam 215 and the normal to the skin surface of the subject. In some embodiments, the at least one predetermined first angle α may be 0°≤α≤30° between the emitted light beam 215 and the normal to the skin surface of the subject. In some embodiments, the light beams may be emitted at a predetermined controlled angle. In some embodiments, the polarized light beams may be emitted at a Brewster angle (θb) relative to the normal to the skin surface 20 of the subject 10, with tan(θb)=2/n1 where n1 and n2 are the refractive indexes of two adjacent layers through which the light beams may pass.

In some embodiments, the light emitted from the at least one light emitting source 120 (e.g. Laser) may be, according to some embodiments, in the Infra-Red or near Infra-Red (IR) spectrum. In some embodiments, Short Wave IR (SWIR) may be utilized for measuring physiological signals from the blood of subject 10. The SWIR waveband runs from the lower edge of the near IR region at 900 nm up to 2500 nm, and may be utilized for inspection of skin, subcutaneous tissue components, blood and blood components in blood vessels of the subject 10. It should be noted that if required, the range of the SWIR waveband may be increased. In some embodiment, each light emitting source 120, or sub-set of light emitting sources 120, may emit light in a different time and/or in a different frequency, such that not all light emitting sources 120 emit light simultaneously. In some embodiment, each light emitting source 120 may emit light in a different polarization.

The measuring unit 200 may include at least one sensor 140, at a predetermined distance (indicated 'd' in FIG. 2) from the at least one light emitting source 120. The sensor 140 may be configured to detect light beams 215 emitted from the at least one light emitting source 120 and reflected from the subject 10. In some embodiments, sensor 140 may be configured to detect light beams for at least one predetermined angle.

In some embodiments, the distance ('d') may correspond to a penetration depth of light beams 215 within the subject's body 10 (for example the distance ('d') may correspond to light beams reflected from a depth of a blood vessel tissue within the body). In some embodiments, the distance ('d') may vary in a way that sensor 140 may detect light beams received at a second angle of βdegrees relative to the normal to the skin surface 20 of the subject (indicated 'β' in FIG. 2). In some embodiments, at least one sensor 140 may be configured to detect light beams emitted from the at least one light emitting source at least one predetermined second angle. In some embodiments, the at least one predetermined second angle may be an angle of 0°≤β<90° (e.g., 0°≤β≤30° between the reflected light beam and the normal to the skin surface 20 of the subject. in some embodiments, the at least one predetermined second angle may be an angle 40°≤β≤50° between the reflected light beam and the normal to the skin surface 20.

According to some embodiments, each sensor 140 may be coupled to at least one polarizer 240 configured to filter out signals detected by sensor 140. In some embodiments, polarizer 240 may be configured to filter the signals having polarization corresponding to the light beams emitted from the at least one light source 120 (e.g., in order to increase the signal to noise ratio). In some embodiments, the polarization of light beams 215 may be altered or changed following an interaction with skin layers dermis tissue 21 or subcutaneous tissue 22 and/or a blood vessel 25. Therefore, in order to filter out light beams 215 that did not interact with the skin layers, polarizer 240 may be configured to filter out signals having the at least one predetermined polarization. Therefore, only light beams 215 that interacted with the skin layers may be detected by the at least one sensor 140.

It should be noted that light beams reflected from the skin 20 (of the subject 10) may maintain the polarization of the emitted light beams, while light beams reflected from dermis tissue 21 or subcutaneous tissue 22 may be (diffusively) reflected with altered polarization. According to some embodiments, polarizer 240 may filter out signals reflected from the skin 20 in order to improve the signal to noise ratio, such that the detected signal corresponds to light beams reflected from dermis tissue 21 or subcutaneous tissue 22 or both.

In some embodiments, more than one polarizer 240 may be coupled to each sensor 140. In some embodiments, when measuring unit 200 includes first and second light emitting sources 120 configured to emit light at a first and second polarization respectively, measuring unit 200 may also include a first polarizer 240 coupled to at least one sensor 140 for filtering the first polarization and a second polarizer 240 coupled to the at least one sensor 140 for filtering the second polarization.

In some embodiments, the polarizer 240 may filter out signals with at least one wire grid. It should be noted that while wire grid is given as an example here, polarizer 240 may include other polarizing elements such as Brewster windows, dichroic polarizers, Birefringence polarizers, and the like.

According to some embodiments, at least one light emitting source 120 may emit light beams 215 in the direction of the skin 20 of the subject 10, to be reflected from dermis tissue 21 or subcutaneous tissue 22 and/or a blood vessel 25 (e.g., by the content of the blood vessel) and then received by at least one sensor 140. In some embodiments, the light beams may be transmitted through the dermis tissue or the subcutaneous tissue (including the blood vessels therein) of the subject 10 and then received by the sensor 140.

It should be noted that with light beams emitted from the at least one light emitting source 120 towards subject 10, the wearable monitoring device 110 may perform optical measuring (e.g. with at least one sensor 140) that are non-invasive to gather measurements. In some embodiments, controller 130 coupled to at least one sensor 140 may analyze the detected data (after filtering out polarized light beams) to gather measurements of the subject.

According to some embodiments, at least one of the emitted light beams 215 and the sensed light beams may be modulated, in order to increase the signal to noise ratio. According to some embodiments, the amount of light with polarization corresponding to the polarization of the at least one light emitting source that is filtered out (e.g., by polarizer 240) may be in the range of 20-50%.

According to some embodiments, the at least one monitoring device 110 may include a controller 130, coupled to the measuring unit 200, and configured to measure and/or analyze physiological signs of the subject 10. In some embodiments, controller 130 may measure and/or analyze physiological signs of the subject 10 based on the detected light beams 215 and also based on at least one predetermined wavelength.

In some embodiments, the monitoring system 100 may further include at least one modulating unit 220 coupled to at least one light emitting source 120, the modulating unit 220 configured to modulate the emitted light beams to a predetermined frequency, intensity and/or polarization. In some embodiments, the modulating unit 220 may be controlled by controller 130.

As may be apparent to one of ordinary skill in the art, light in specific wavelengths between 400-2500 nm (e.g. 417 nm, 545 nm, or 578 nm), reflected from different tissue depths have different intensities. In some embodiments, light in specific wavelengths between 400-2500 nm that are reflected from dermis tissue and/or subcutaneous tissue and/or reflected from a blood vessel may have different intensities. According to some embodiments, it may be possible to determine a light intensity threshold based on the reflection readings in one or more sensors 140, wherein the position of the measuring unit 200 being over a blood vessel may be determined according to the determined threshold so that when the reflected light has an intensity that is higher/lower than the threshold the measuring unit 200 may be over a blood vessel.

In some embodiments, the monitoring system 100 may further include positioning correction indicators that are adapted to allow the user to correctly place measuring unit 200 over a blood vessel. For instance, displaying to the user how to move monitoring device 110 to improve positioning of light emitting source 120 and/or sensor 140 to optimize reflections to the sensor.

In some embodiments, the difference in the data between the emitted beam and the received (reflected) beam may provide an indication on the radiation (e.g., light) absorption by the blood in blood vessel 25 and thus may indicate characteristics and blood measurements of the blood inside blood vessel 25, in a non-invasive procedure. In some embodiments, each light emitting source 120 may be provided with an optical collimator (or reflector) so as to allow directing the light beam emitted by each light source 120 in a specific predefined direction.

Figure 3:
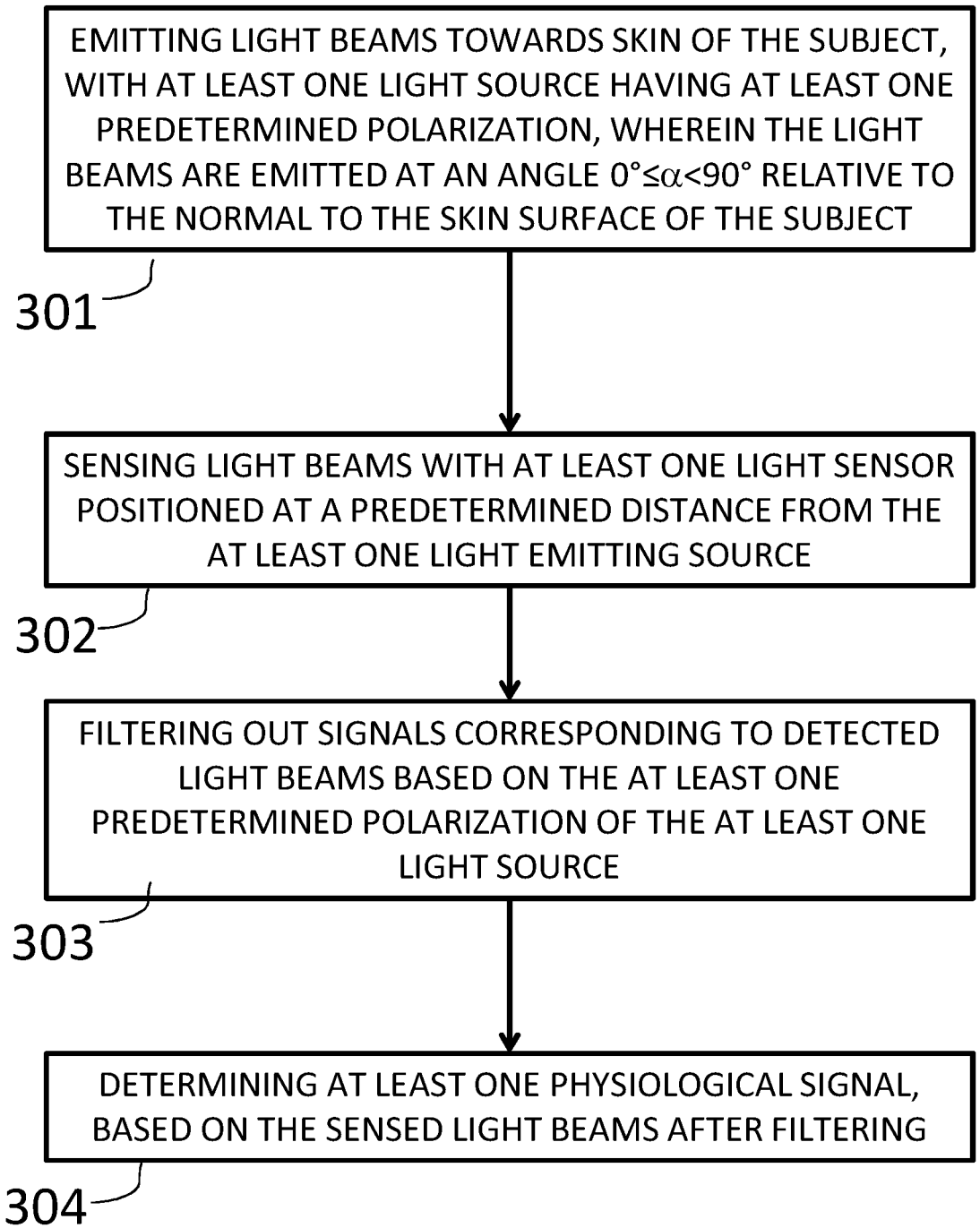
FIG. 3 shows a flow chart for a method of non-invasive monitoring of physiological measurements of a subject, according to some embodiments of the invention.

Reference is now made to FIG. 3, which shows a flow chart for a method of non-invasive monitoring of physiological measurements of a subject, according to some embodiments of the invention. The method of FIG. 3 may be performed by monitoring device 110 and/or system 100. In some embodiments, light beams may be emitted 301 towards the skin 20 of the subject, with at least one light source (such as light emitting source 120 shown in FIG. 2) having a predetermined polarization, wherein the light beams are emitted at an angle $0°\leq\alpha<90°$ relative to the normal to the skin surface 20 of the subject. In some embodiments, emitting the light beams may be from a first light source having a first polarization and a second light source having a second polarization.

In some embodiments, light beams may be sensed 302 with at least one light sensor (such as sensor 140 shown in FIG. 2) positioned at a predetermined distance "d" from the at least one light emitting source 120. In some embodiments, the sensing is carried out using beams reflected from the skin at an angle $0°\leq\beta90°$ relative to the normal to the skin surface 20 of the subject, as illustrated in FIG. 2. In some embodiments, when the light beams are emitted at the first and second polarization the beams may be sensed by one or more light sensor (e.g., sensor 140) configured to detect light at the first polarization and the second polarization.

In some embodiments, signals may be filtered out 303 corresponding to detected light beams based on the at least polarization of the at least one light source 120. In some embodiments, filtering out signals may include filtering signals having the at least one predetermined polarization. In some embodiments, at least one physiological signal may be determined 304 based on the sensed light beams after filtering, for instance such that only signals that pass the filtering may be analyzed. In some embodiments, the sensed light beams pass through at least one of epidermis, dermis, subcutaneous tissue and blood vessel of the subject.

In some embodiments, an alert may be issued upon detection of a change (e.g., in time) in measured physiological signals exceeding a predetermined threshold. In some embodiments, two consecutive measurements may be compared to detect a change thereof, for example a change in measured value may indicate a dangerous rise in a blood substance (e.g., a rise in glucose).

According to some embodiments, sampling of the physiological signals of the subject may be carried out repetitively every predefined time period. In some embodiments, a first wavelength may be used for a first measured physiological characteristic, and a second wavelength may be used for a second measured physiological characteristic. In some embodiments, intensities of light beams detected by the at least one light sensor may be calibrated (e.g., in laboratory conditions), such that the detected light beams may be reflected from a known blood vessel and detected thereon.

Unless explicitly stated, the method embodiments described herein are not constrained to a particular order in time or chronological sequence. Additionally, some of the described method elements may be skipped, or they may be repeated, during a sequence of operations of a method.

Various embodiments have been presented. Each of these embodiments may of course include features from other embodiments presented, and embodiments not specifically described may include various features described herein.

The invention claimed is:

1. A method of non-invasive monitoring of physiological measurements of a subject, the method comprising:
    emitting light beams towards a skin of the subject, with at least one light source having at least one predetermined polarization, wherein the light beams are emitted at an angle $0°<a<90°$ relative to the normal to the skin surface of the subject;
    sensing light beams with at least one light sensor positioned at a predetermined distance "d" from the at least one light source;
    filtering out signals corresponding to detected light beams based on the at least one predetermined polarization of the at least one light source; and
    determining at least one physiological signal, based on the sensed light beams after filtering,
    wherein the sensed light beams pass through at least one of epidermis, dermis, subcutaneous tissue and blood vessel of the subject, and
    wherein the predetermined distance "d" corresponds to a penetration depth of light beams within the subject.

2. The method of claim 1, wherein emitting the light beams is from a first light source having a first polarization and a second light source having a second polarization.

3. The method of claim 2, wherein sensing light beams is with one or more light sensor configured to detect light at the first polarization and the second polarization.

4. The method of claim 1, wherein the sensing is carried out at an angle $0°<\beta<90°$ relative to the normal to the skin surface of the subject.

5. The method of claim 1, further comprising modulating at least one of the emitted light beams and the sensed light beams to a predetermined frequency.

6. The method of claim 1, wherein filtering out signals comprises filtering signals having the at least one predetermined polarization.

7. The method of claim 1, comprising emitting light beams in at least one predetermined wavelength, wherein determining the at least one physiological signal is also based on the at least one predetermined wavelength.

8. The method of claim 1, further comprising comparing at least two consecutive measurements to detect a change.

9. The method of claim 1, further comprising calibrating intensities of light beams detected by the at least one light sensor, wherein the detected light beams are reflected from a known blood vessel and detected thereon.

10. The method of claim 1, further comprising positioning the at least one of light sensor and light source over a known blood vessel.

11. The method of claim 1, further comprising controlling the polarization of the emitted light beams.

12. The method of claim 1, further comprising issuing an alert upon detection of a change in measured physiological signals exceeding a predetermined threshold.

* * * * *